(12) United States Patent
Doyle et al.

(10) Patent No.: US 12,384,825 B2
(45) Date of Patent: Aug. 12, 2025

(54) MONOMERIC PEPTIDE MULTI-AGONIST TARGETING THE GLP1 RECEPTOR AND NPY RECEPTORS

(71) Applicant: Syracuse University, Syracuse, NY (US)

(72) Inventors: Robert P. Doyle, Manlius, NY (US); Brandon Milliken, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 805 days.

(21) Appl. No.: 17/600,221

(22) PCT Filed: Apr. 1, 2020

(86) PCT No.: PCT/US2020/026068
§ 371 (c)(1),
(2) Date: Sep. 30, 2021

(87) PCT Pub. No.: WO2020/205909
PCT Pub. Date: Oct. 8, 2020

(65) Prior Publication Data
US 2022/0204581 A1    Jun. 30, 2022

Related U.S. Application Data

(60) Provisional application No. 62/827,229, filed on Apr. 1, 2019.

(51) Int. Cl.
*C07K 14/575* (2006.01)
*A61K 38/00* (2006.01)
*C12N 15/62* (2006.01)

(52) U.S. Cl.
CPC ............ *C07K 14/575* (2013.01); *C12N 15/62* (2013.01); *A61K 38/00* (2013.01)

(58) Field of Classification Search
None
See application file for complete search history.

(56) References Cited

U.S. PATENT DOCUMENTS 10,111,932 B2 * 10/2018 Doyle ............... A61K 38/2271
2018/0271947 A1   9/2018 Doyle et al.

FOREIGN PATENT DOCUMENTS

WO    WO2005077072 A2    8/2005

OTHER PUBLICATIONS

Patent Cooperation Treaty, International Search and Written Opinion dated Aug. 27, 2020, ISA/US (USPTO).
International Preliminary Report on Patentability for Application No. PCT/US2020/026068, mailed Oct. 14, 2021.
Chepurny et al., Chimeric peptide EP45 as a dual agonist at GLP-1 and NPY2R receptors. Sci Rep. Feb. 28, 2018;8(1):3749. doi: 10.1038/s41598-018-22106-1. Erratum in: Sci Rep. Apr. 13, 2018;8(1):6192. doi: 10.1038/s41598-018-24359-2.
Milliken et al., Design and Evaluation of Peptide Dual-Agonists of GLP-1 and NPY2 Receptors for Glucoregulation and Weight Loss with Mitigated Nausea and Emesis. J Med Chem. Jan. 28, 2021;64(2):1127-1138. doi: 10.1021/acs.jmedchem.0c01783. Epub Jan. 15, 2021.
Sweet et al., Regulation of ATP/ADP in pancreatic islets. Diabetes. Feb. 2004;53(2):401-9. doi: 10.2337/diabetes.53.2.401.

* cited by examiner

*Primary Examiner* — Lianko G Garyu
*Assistant Examiner* — Tara L Martinez
(74) *Attorney, Agent, or Firm* — Wolf, Greenfield & Sacks, P.C.

(57) ABSTRACT

A series of chimeric peptides that provide a mechanism for obesity treatment concomitant with T2DM in the form of dual agonism of the anorectic neuropeptide Y-receptor (Y2-R) and the glucoregulatory receptor GLP1-R. Preliminary results show that, dependent on the selected peptide, once-daily administration suppress FI in male and female rats can be reduced to 12-65% compared to baseline conditions before treatment, dependent on dose and age of animals, and glucose tolerance can be improved as well. Peptides also demonstrated Y1-receptor agonism, conferring protection on beta-islet cells against inflammatory damage. The peptides were designed by targeting serial anorectic pathways simultaneously and are promising candidates for modulating FI and glucoregulation in an efficacious and safe way.

9 Claims, 16 Drawing Sheets

Specification includes a Sequence Listing.

| Peptide | Sequence | Sequence ID |
|---|---|---|
| PYY$_{1-36}$ | YPIKPEAPGEDASPEELNRYYASLRHYLNLVTRQRY-NH2 | SEQ ID NO: 1 |
| PYY$_{3-36}$ | IKPEAPGEDASPEELNRYYASLRHYLNLVTRQRY-NH2 | SEQ ID NO: 2 |
| GLP-1 | HAEGTFTSDVSSYLEGQAAKEFIAWLVKG | SEQ ID NO: 3 |
| Ex-4 | HGEGTFTSDLSKQMEEEAVRLFIEWLKNGGPSSGAPPPS | SEQ ID NO: 4 |
| EP38 (I) | HGEGTFTSDLSKQMEEEAVRLFIEWLKNGGPSS------------TRQRY-NH$_2$ | SEQ ID NO: 5 |
| EP45 (II) | HGEGTFTSDLSKQINEEEAVRLFIEWLKNGGPS----------RHYLNLVTRQRY-NH$_2$ | SEQ ID NO: 6 |
| EP40 (III) | HSQGTFTSDLSKQINEEEAVRLFIEWLKN---------RHYLNLVTRQRY-NH$_2$ | SEQ ID NO: 7 |
| EP44 (IV) | HSQGTFTSDLSKQINEEEAVRLFIEWLKNGGPS--------RHYLNLVTRQRY-NH$_2$ | SEQ ID NO: 8 |
| EP46 (V) | HSQGTFTSDLSKQMEEEAVRLFIEWLKN--------RYYASLRRHYLNLVTRQRY-NH$_2$ | SEQ ID NO: 9 |
| EP50 (VI) | HSQGTFTSDLSKQINEEEAVRLFIEWLKNGGPSRYYASLRRHYLNLVTRQRY-NH$_2$ | SEQ ID NO: 10 |
| GEP44 (VII) | HsQGTFTSDLSKYLEEEAVREFIAWLKNGGPS--------RHYLNLVTRQRY-NH$_2$ | SEQ ID NO: 11 |

FIG. 2

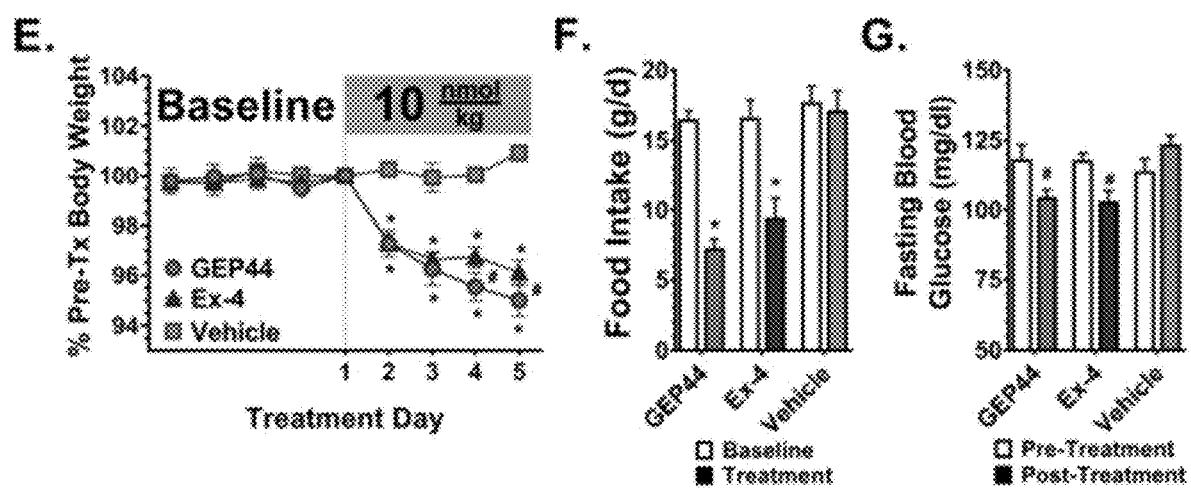
FIG. 9E, 9F, and 9G

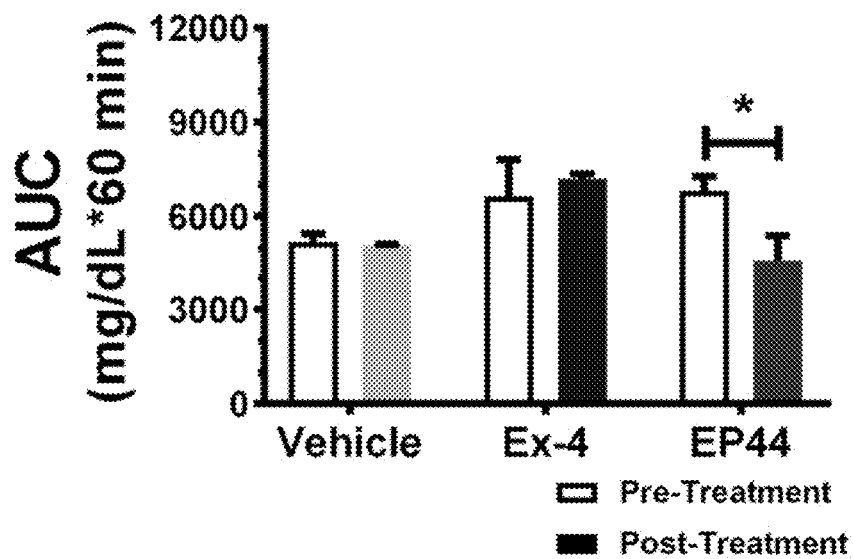
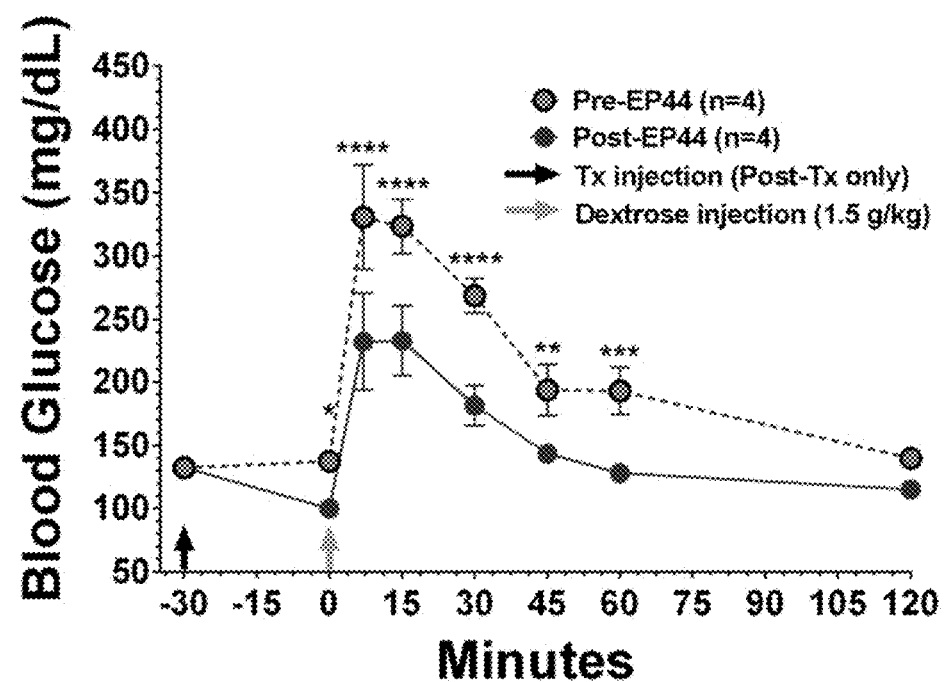
FIG. 10

SEQUENCE LISTING

```
<160> NUMBER OF SEQ ID NOS: 11

<210> SEQ ID NO 1
<211> LENGTH: 36
<212> TYPE: PRT
<213> ORGANISM: Homo sapiens

<400> SEQUENCE: 1

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35
```

```
<210> SEQ ID NO 2
<211> LENGTH: 34
<212> TYPE: PRT
<213> ORGANISM: Homo sapiens

<400> SEQUENCE: 2

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 3
<211> LENGTH: 29
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 4
<211> LENGTH: 39
<212> TYPE: PRT
<213> ORGANISM: Homo sapiens

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 38
<212> TYPE: PRT
<213> ORGANISM: Artificial Sequence
<220> FEATURE:
<223> OTHER INFORMATION: chimeric peptide

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Thr Arg Gln Arg Tyr
        35

<210> SEQ ID NO 6
<211> LENGTH: 45
<212> TYPE: PRT
<213> ORGANISM: Artificial Sequence
<220> FEATURE:
<223> OTHER INFORMATION: chimeric peptide

<400> SEQUENCE: 6

His Gly Glu Gly Thr Phe Thr Ser Asp Leu Ser Lys Gln Ile Asn Glu
1               5                   10                  15
```

```
Glu Glu Ala Val Arg Leu Phe Ile Glu Trp Leu Lys Asn Gly Gly Pro
            20                  25                  30

Ser Arg His Tyr Leu Asn Leu Val Thr Arg Gln Arg Tyr
        35                  40                  45

<210> SEQ ID NO 7
<211> LENGTH: 41
<212> TYPE: PRT
<213> ORGANISM: Artificial Sequence
<220> FEATURE:
<223> OTHER INFORMATION: chimeric peptide

<400> SEQUENCE: 7

His Ser Gln Gly Thr Phe Thr Ser Asp Leu Ser Lys Gln Ile Asn Glu
1               5                   10                  15

Glu Glu Ala Val Arg Leu Phe Ile Glu Trp Leu Lys Asn Arg His Tyr
            20                  25                  30

Leu Asn Leu Val Thr Arg Gln Arg Tyr
        35                  40

<210> SEQ ID NO 8
<211> LENGTH: 45
<212> TYPE: PRT
<213> ORGANISM: Artificial Sequence
<220> FEATURE:
<223> OTHER INFORMATION: chimeric peptide

<400> SEQUENCE: 8

His Ser Gln Gly Thr Phe Thr Ser Asp Leu Ser Lys Gln Ile Asn Glu
1               5                   10                  15

Glu Glu Ala Val Arg Leu Phe Ile Glu Trp Leu Lys Asn Gly Gly Pro
            20                  25                  30

Ser Arg His Tyr Leu Asn Leu Val Thr Arg Gln Arg Tyr
        35                  40                  45

<210> SEQ ID NO 9
<211> LENGTH: 47
<212> TYPE: PRT
<213> ORGANISM: Artificial Sequence
<220> FEATURE:
<223> OTHER INFORMATION: chimeric peptide

<400> SEQUENCE: 9

His Ser Gln Gly Thr Phe Thr Ser Asp Leu Ser Lys Gln Met Glu Glu
1               5                   10                  15

Glu Ala Val Arg Leu Phe Ile Glu Trp Leu Lys Asn Arg Tyr Tyr Ala
            20                  25                  30

Ser Leu Arg Arg His Tyr Leu Asn Leu Val Thr Arg Gln Arg Tyr
        35                  40                  45

<210> SEQ ID NO 10
<211> LENGTH: 52
<212> TYPE: PRT
<213> ORGANISM: Artificial Sequence
<220> FEATURE:
<223> OTHER INFORMATION: chimeric peptide

<400> SEQUENCE: 10

His Ser Gln Gly Thr Phe Thr Ser Asp Leu Ser Lys Gln Ile Asn Glu
1               5                   10                  15

Glu Glu Ala Val Arg Leu Phe Ile Glu Trp Leu Lys Asn Gly Gly Pro
            20                  25                  30
```

```
Ser Arg Tyr Tyr Ala Ser Leu Arg Arg His Tyr Leu Asn Leu Val Thr
        35                  40                  45

Arg Gln Arg Tyr
    50

<210> SEQ ID NO 11
<211> LENGTH: 44
<212> TYPE: PRT
<213> ORGANISM: Artificial Sequence
<220> FEATURE:
<223> OTHER INFORMATION: chimeric peptide

<400> SEQUENCE: 11

His Ser Gln Gly Thr Phe Thr Ser Asp Leu Ser Lys Tyr Leu Glu Glu
1               5                   10                  15

Glu Ala Val Arg Glu Phe Ile Ala Trp Leu Lys Asn Gly Gly Pro Ser
            20                  25                  30

Arg His Tyr Leu Asn Leu Val Thr Arg Gln Arg Tyr
        35                  40
```

MONOMERIC PEPTIDE MULTI-AGONIST TARGETING THE GLP1 RECEPTOR AND NPY RECEPTORS

CROSS-REFERENCE TO RELATED APPLICATIONS

The present application claims priority to U.S. Provisional Application No. 62/827,229, filed on Apr. 1, 2019.

BACKGROUND OF THE INVENTION

1. Field of the Invention

The present invention relates to pharmaceuticals for treatment of diabetes and obesity and, more specifically, to peptides that can regulate appetite and blood glucose without negative gastrointestinal side effects.

2. Description of the Related Art

Glucagon-like peptide-1 receptor agonists (GLP1RAs), are potent stimulators of glucose-dependent insulin secretion, while also modulating satiety and energy intake. Treatment with a GLP-1RA also induces appetite suppression as evidenced by food intake reduction and body weight loss. Few treatments for type 2 diabetes mellitis (T2DM) and obesity achieve meaningful long-term weight-loss however, and, importantly, the hypophagic effects of all known GLP-1RAs are accompanied by nausea and vomiting (affecting ~20-50% of patients), leading to discontinuation of drug treatment in ~6-10% and reduced dose tolerance in another ~15% of patients. Thus, there is a critical need for a new generation of obesity medications that provide glycemic control with enhanced hypophagic response, without nausea/emesis. Another critical unmet need in the treatment of T2DM is protection against β-islet cell mass loss, which is associated with the cytokine storm evident in diabetes.

BRIEF SUMMARY OF THE INVENTION

The present invention comprises a series of chimeric peptides that provide a mechanism for profound weight loss concomitant with T2DM management and/or reduction of disease progression in the form of multi agonism of gut hormone receptors in the form of the anorectic neuropeptide Y2-receptor (Y2-R), the islet protecting neuropeptide Y1-receptor (Y1-R) and the glucoregulatory receptor Glugacon-Like Peptide-1 receptor (GLP1-R). Preliminary results show that, dependent on the selected peptide, once-daily administration suppress FI in male and female rats up to ~82%, compared to baseline conditions before treatment, dependent on dose and age of animals, and glucose tolerance can be improved as well. The peptides were designed by targeting serial anorectic pathways simultaneously and are promising candidates for modulating FI and glucoregulation in an efficacious and safe way.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 2 is a chart of exemplary sequences for chimeric peptides according to the present invention along with the sequences of various controls;

Figure 11:
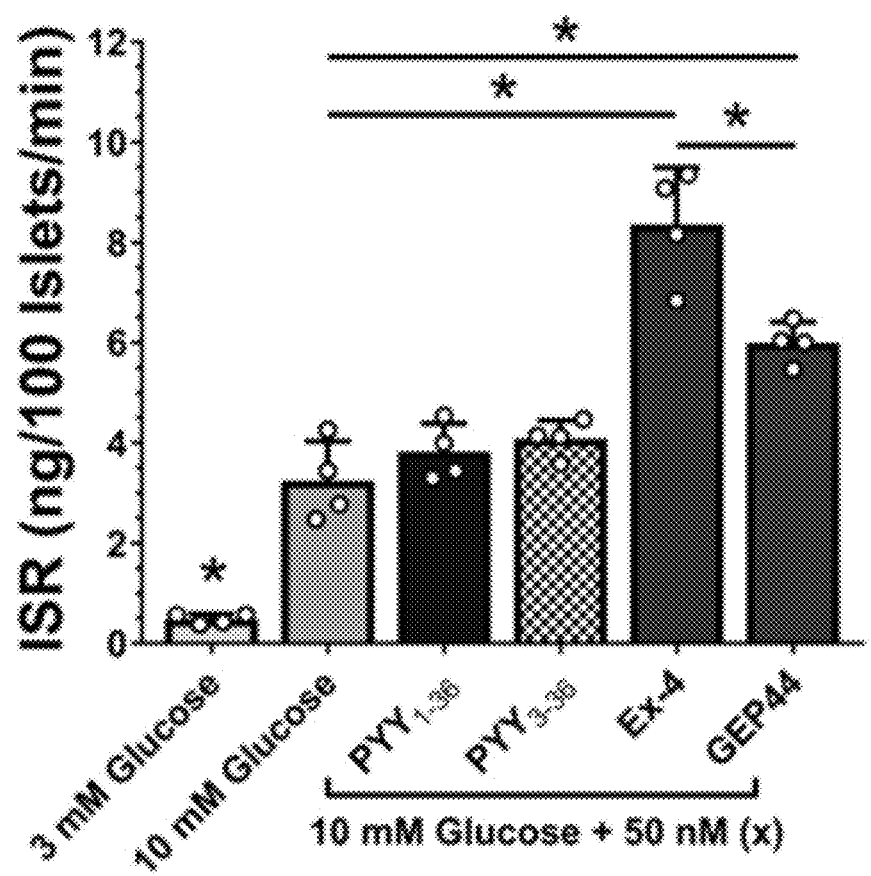
Figure 12:
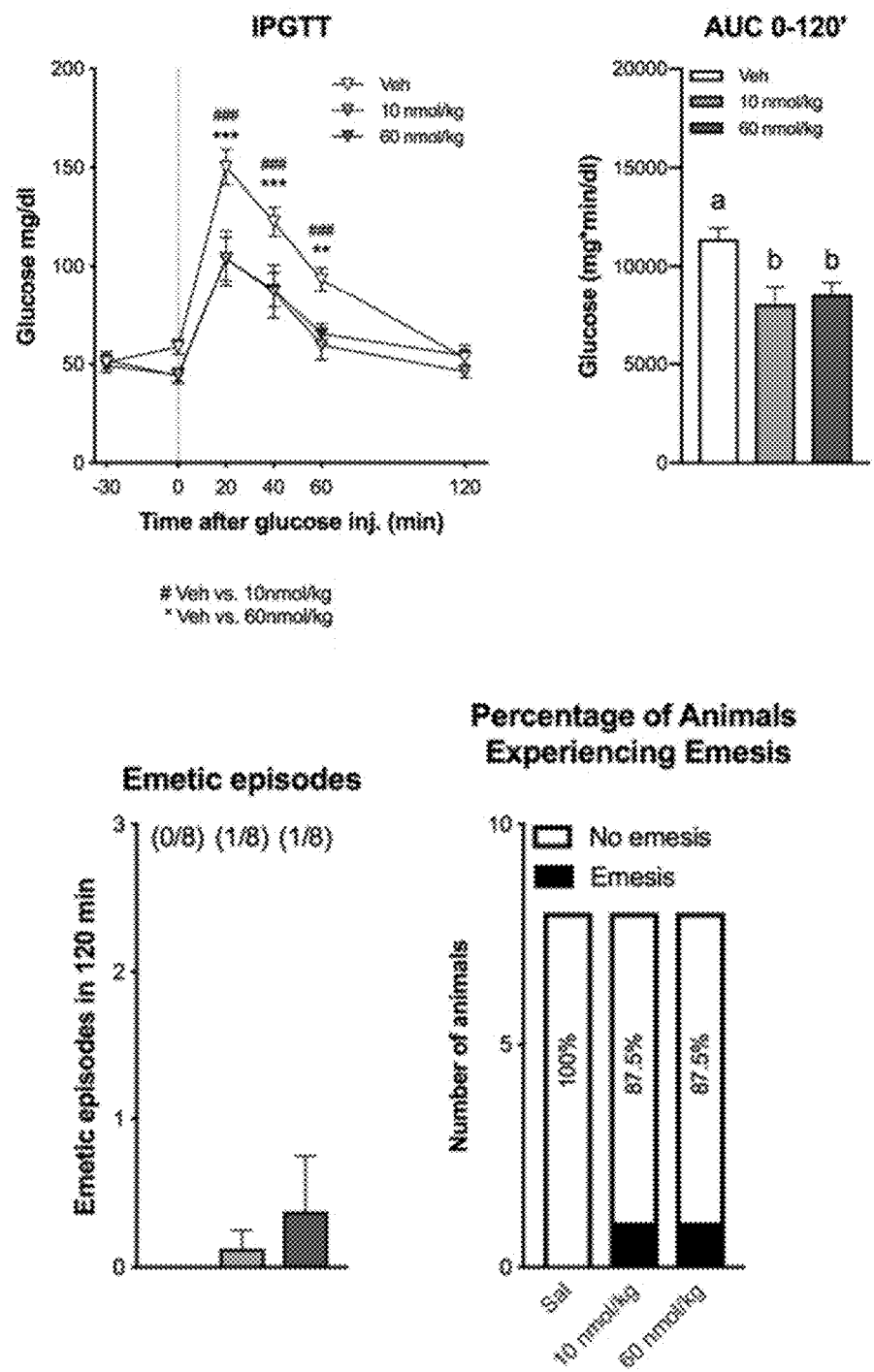
Figure 13:
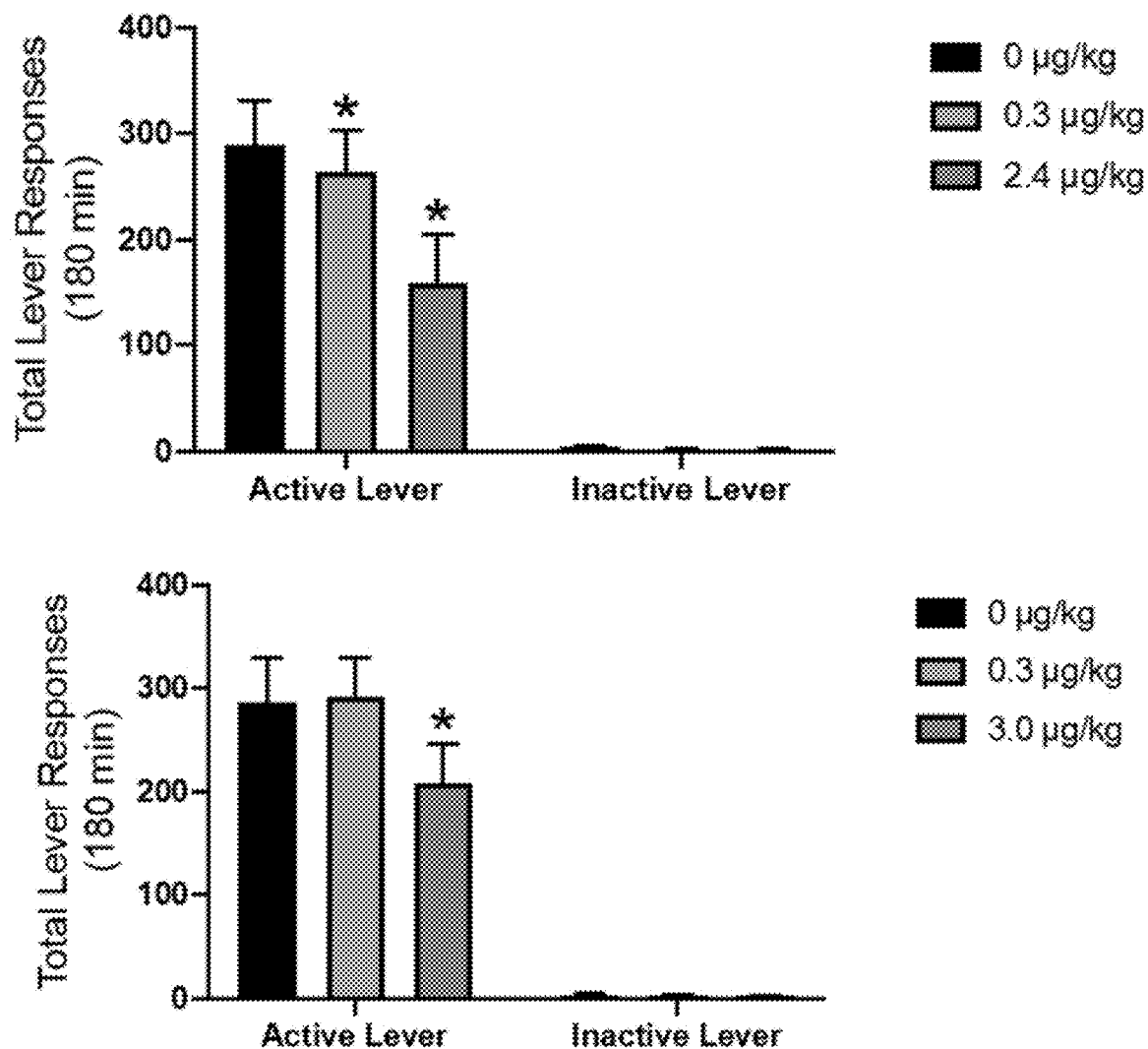

FIG. 9A through 9I is a series of graphs of a dose escalation study averaging food intake for 2-d on each dose showing robust reduction of food intake in response to GEP44 without induction of nausea assessed by kaolin intake (FIG. 9A) vs. Ex4 (FIG. 9B); the dose responses of cumulative 24-h food intake following GEP44 (FIG. 9C) and Ex4 (FIG. 9D) averaged over 2-d of treatment, n=4-5 lean adult male rats/gr, a longitudinal study in diet-induced obese rats shows sustained weight loss (FIG. 9E), reduced food intake (FIG. 9F), and reduced fasting blood glucose (FIG. 9G) due to GEP44 treatment, and stronger reductions in blood glucose during intraperitoneal glucose tolerance testing following 5-d treatments with GEP44 (FIG. 9H) vs. Ex4 (FIG. 9I) in pre-diabetic rats, with n=3-5 per group. $\#p<0.05$, $*p<0.001$;

FIG. 10 is a series of graphs of a reduction of fasting blood glucose levels in obese male rats (726±33 g pre-treatment) receiving EP44 (2 d, 10 nmol/kg/d) compared to 2 days before drug treatment with saline injections; and FIG. 11 is a graph of the stimulation of glucose dependent static insulin secretion (GSIS), recorded as insulin secretion rate (ISR), in rat islets in response to 10 mM glucose and 50 nM peptides, as indicated. Ex4 and GEP44 both stimulated GSIS, while PYY1-36 and PYY3-36 did not;

FIG. 12 is a series of graphs showing administration of GEP44 in shrews confirmed glucoregulation (IPGTT) and demonstrates little/no vomiting (emesis);

FIG. 13 is a series of graphs showing testing of GEP44 in rats showing a reduction in the drive to obtain fentanyl when provided at doses lower than exendin-4.

DETAILED DESCRIPTION OF THE INVENTION

Figure 1:
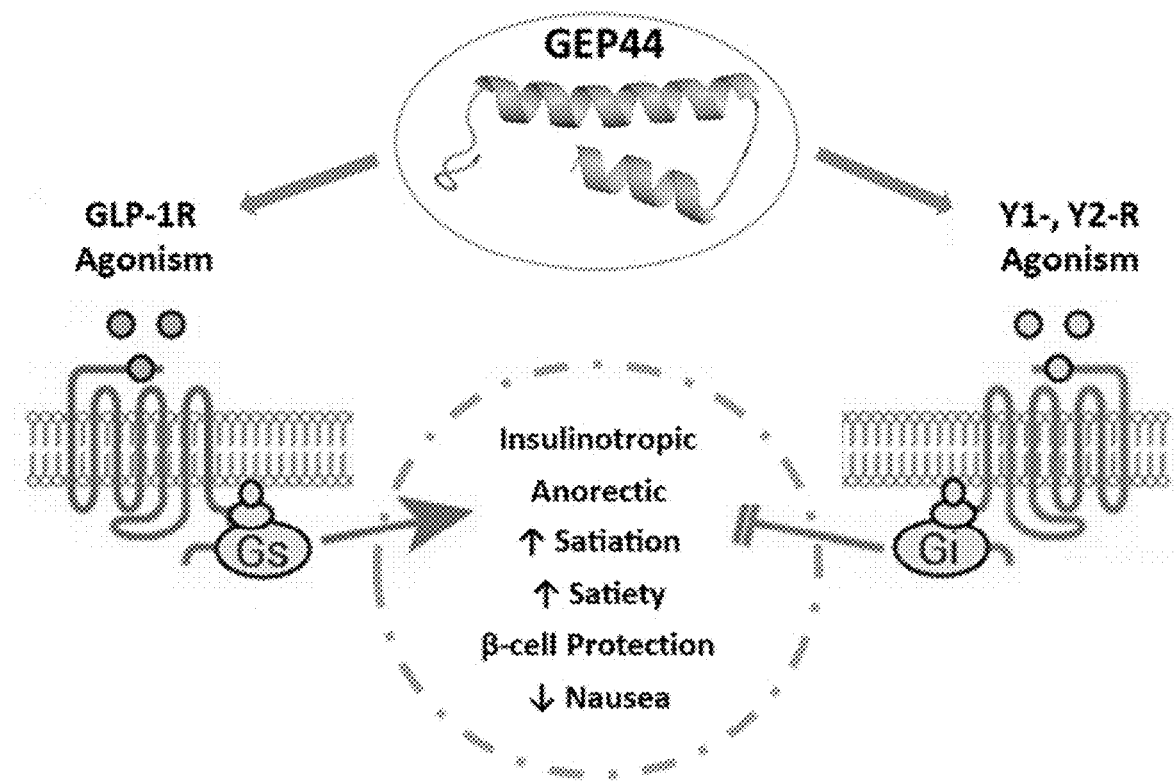
FIG. 1 is a schematic of a chimeric peptide according to the present invention.

Referring to the figures, wherein like numeral refer to like parts throughout, there is seen in FIG. 1 a schematic of a chimeric peptide (GEP44) (SEQ ID NO: 11) according to the present invention. Several other new monomeric chimeric peptides as seem in FIG. 2. Chimeric peptides are single peptides containing amino acid motifs from different peptides.

Compelling data of an initial novel once-daily peptide EP38 (SEQ ID NO: 5) demonstrated significantly improved reduction of FI and BW gain at comparable doses to exendin-4 (SEQ ID NO: 4) (Ex-4; a GLP-1RA). The rational approach of continued improvement of peptide design led to the development of an exemplary peptide referred to as EP44 (SEQ ID NO: 8), as seen in FIG. 2, which potently reduced blood glucose levels (30 min glucose during glucose tolerance testing: 269 mg/dL pre-treatment, 181 mg/dL after five once-daily 10 nmol/kg EP44 doses), without inducing nausea (by kaolin intake, tested up to 90 nmol/kg) or reducing FI; while FI reduction occurred at 2-d treatments with daily injections of higher doses (2-d avg. FI: −15% at 30 nmol/kg/d; −28% at 90 nmol/kg/d).

Figure 3:
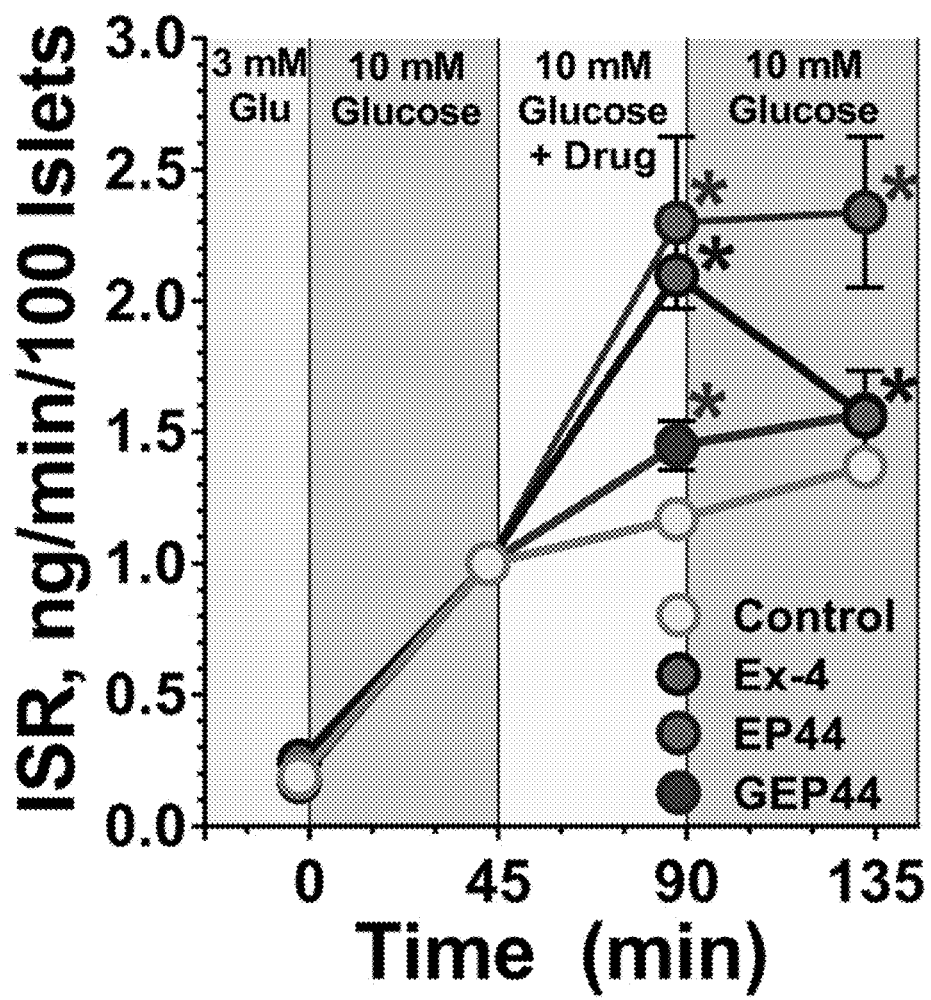
FIG. 3 is a graph of the acute effects of Ex-4, EP44 and GEP44 exposure and washout on insulin secretion in rat islet cell perifusion, showing that the effects of EP44 and GEP44 were more sustained vs. Ex-4. $*p<0.05$.
Figure 4:
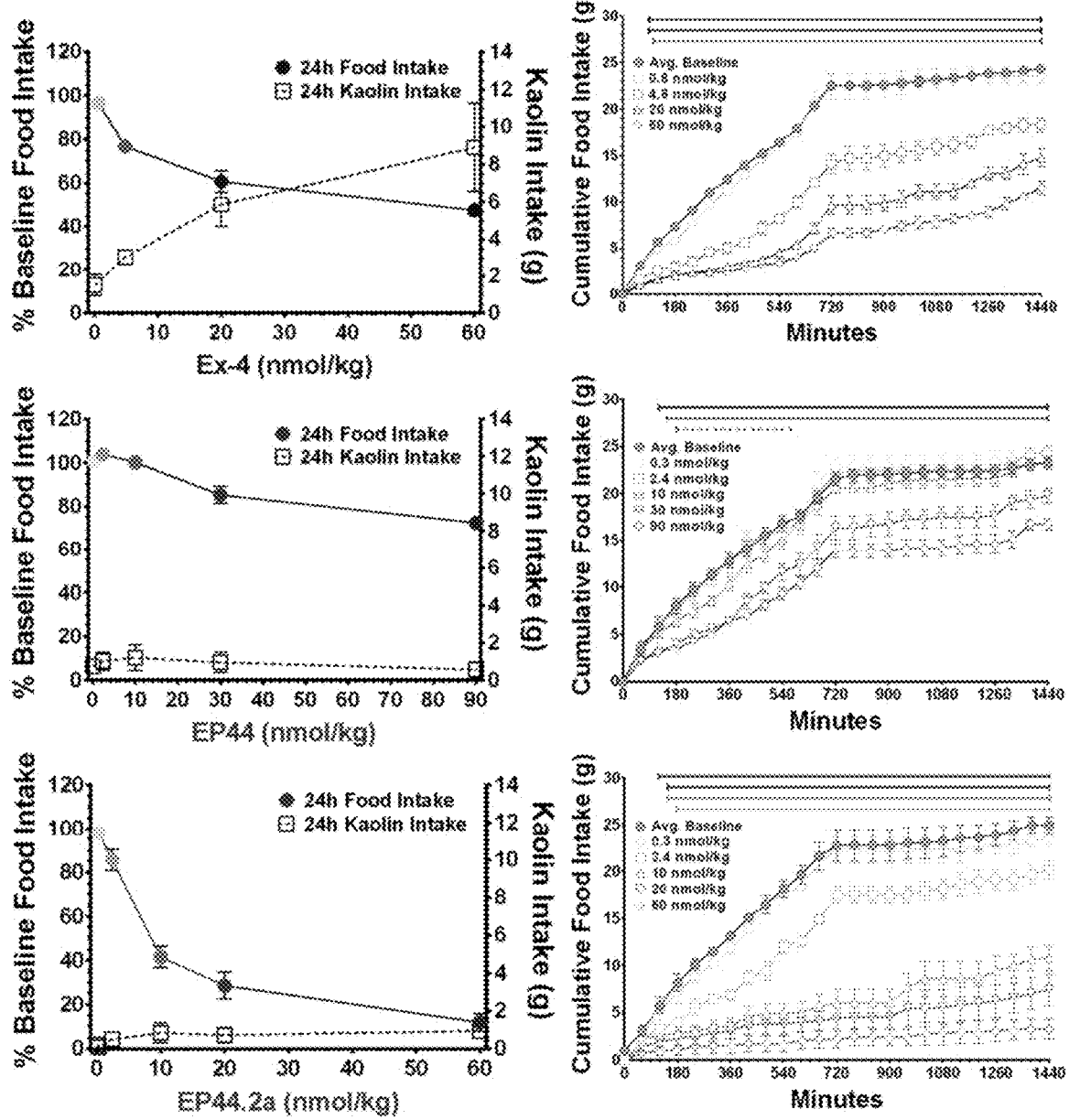
FIG. 4 is a series of graphs of the robust reduction of FI in response to GEP44 without induction of nausea assessed by kaolin intake (C) vs. Ex-4 (A) or EP44 (B), with the dose responses of cumulative FI following Ex-4 (D), EP44 (E) and GEP44 (F)

Further optimization of EP44 resulted in GEP44, also seen in FIG. 2, which is a potent agonist of Y2-R ($EC_{50}$ 10 nM; compared to 16 nM for native $PYY_{3-36}$, implying improved ligand design at the Y2-R) and GLP-1R ($EC_{50}$ 300 μM), capable of stimulating insulin release in human islets, as seen in FIG. 3, and exhibiting potent anorectic effects (2-d avg. FI: −58% at 10 nmol/kg/d; −84% at 30 nmol/kg/d in rats) without induction of nausea, as seen in FIG. 4. Table 1 below shows the dose-response nonlinear regression of peptides at the GLP-1R (tracking cAMP stimulation via FRET at EPAC2) and both the Y1- and Y2-R (tracked by mitigation of adenosine stimulated cAMP at the A2b receptor via FRET at EPAC2). $EC_{50}$ values are the result of at least triplicate data sets and n/a refers to not applicable.

| Peptide | $EC_{50}$ GLP1R | $EC_{50}$ Y2R | $EC_{50}$ Y1R |
| --- | --- | --- | --- |
| $PYY_{1-36}$ | n/a | n/a | 12 nM |
| $PYY_{3-36}$ | n/a | 16 nM | n/a |
| Ex4 | 16 pM | n/a | n/a |
| EP38 | 80 pM | >300 nM | n/a |
| EP45 | 473 pM | 47 nM | n/a |
| EP40 | 337 pM | 61 nM | >100 nM |
| EP44 | 240 pM | 32 nM | >100 nM |
| EP46 | 28 nM | 18 nM | >300 nM |
| EP50 | 2.3 nM | 25 nM | >300 nM |
| GEP44 | 330 pM | 10 nM | 24 nM |

Figure 5:
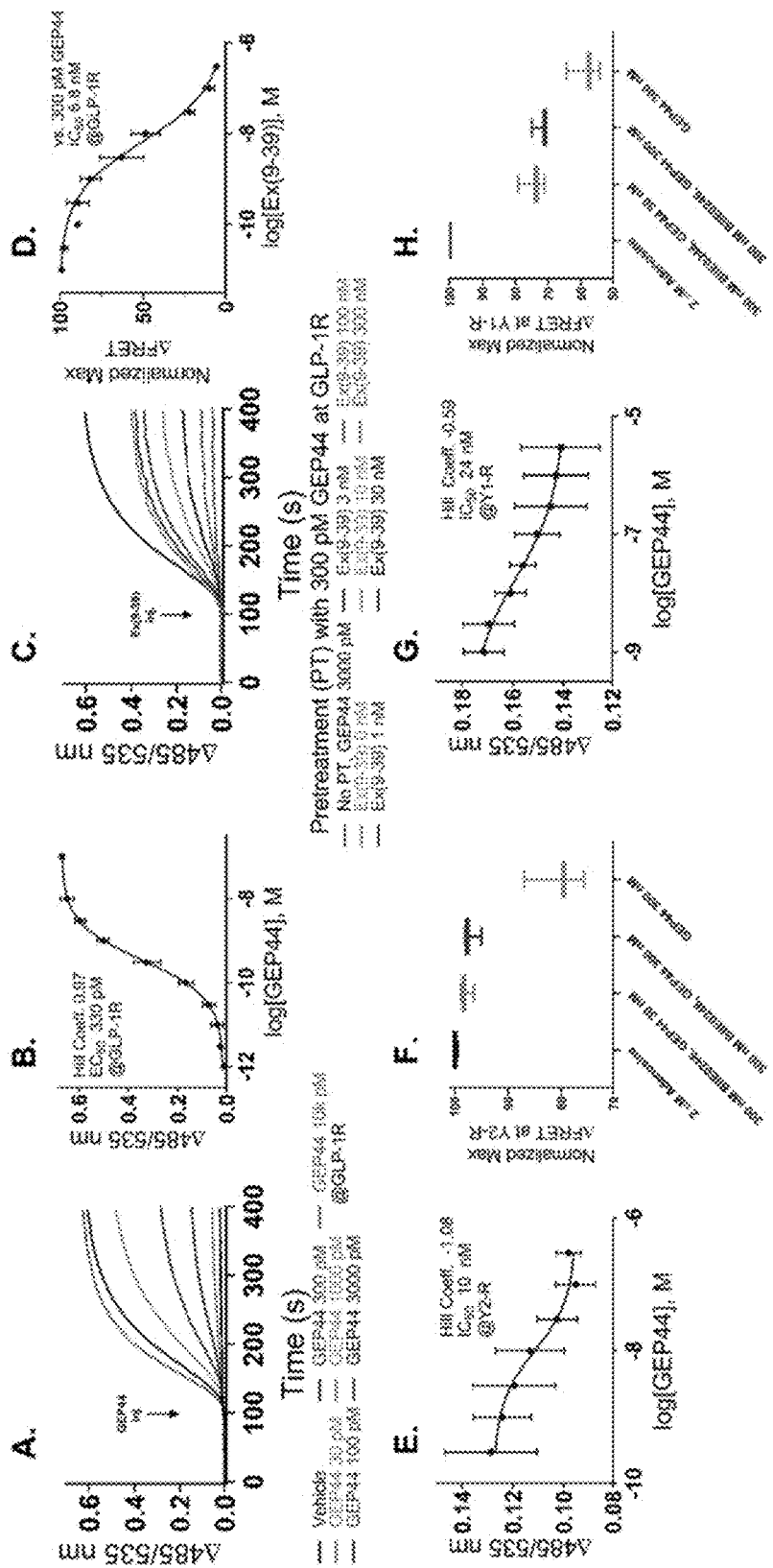
FIG. 5 is a series of graphs showing that the Y1-R (partial) and Y2-R (potent) antagonist BIIE0246 blocked GEP44 agonism in FRET assays in cells expressing each receptor.

In addition, agonism ($EC_{50}$ 83 nM; relative to 42 nM $PYY_{1-36}$ control in the same assay) of the Y1-R was also noted for GEP44, a receptor known to be present in human and rat islets (unlike Y2-R). This result was expected based on the fact that both Y1-R and Y2-R native ligands ($PYY_{1-36}$ and $PYY_{3-36}$, respectively), differ only in the initial N-terminal YP dipeptide sequence of $PYY_{1-36}$. Given the identical C-terminal region of both peptides is found in GEP44, some interaction and agonism was clearly possible at Y1-R. To further confirm this receptor selective agonism, it was also demonstrated that the Y1-R (partial) and Y2-R (potent) antagonist BIIE0246 blocked GEP44 agonism in FRET assays in cells expressing each receptor individually, as seen in FIG. 5.

Figure 6:
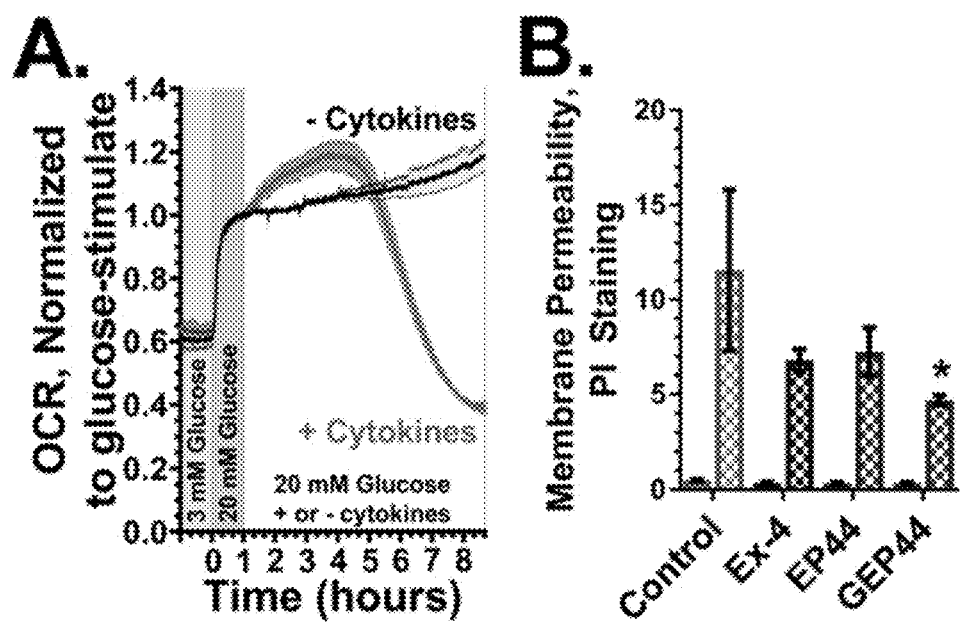
FIG. 6 is a graph of the effect of IFN-γ, TNF-α, and IL-10 on OCR of perifused isolated rat islets, where (A) shows an increase in membrane permeability as a marker of cell damage by cytokines and prevention by GEP44 and (B) shows a baseline condition with: small solid bars; added cytokines: patterned bars. $*p<0.05$.

Recent evidence points to a protective effect of Y1-R agonism in β-cells, a critical unmet need in current treatment of T2DM. Assay of cytokine (IL-1β, TNF-α, IFN-γ) induced islet apoptosis will test whether pretreatment with chimeric peptides can result in β-cell protection (see FIG. 6 that supports such for GEP44). Overall, these data support that GEP44 is an extraordinary lead candidate for achieving polypharmacy in the form of glucoregulation coupled with profound weight loss, potential β-cell mass protection, and reduced/mitigated nausea/emesis. The peptides of the present invention thus provide a mechanism for obesity treatment concomitant with T2DM in the form of dual agonism of the anorectic neuropeptide Y-receptor (Y2-R) and the glucoregulatory receptor GLP1-R.

Preliminary results showed that, dependent on the selected novel agonist, once-daily administration suppress FI in male and female rats can be reduced to 12-65% compared to baseline conditions before treatment, dependent on dose and age of animals, and glucose tolerance can be improved as well. Utilizing a novel concept of targeting serial anorectic pathways simultaneously with novel single-small molecule peptides are promising and relevant to the mission of the NIDDK, as the data demonstrates the validity of modulating FI and glucoregulation in an efficacious and safe way. More specifically, GEP44 is a potent multi-agonist of Y2-R and GLP1-R, capable of exhibiting potent anorectic effects (2-d avg. FI: −58% at 10 nmol/kg/d; −84% at 30 nmol/kg/d in rats) without induction of nausea at anorectic doses, also stimulating insulin release in human islets. In addition, agonism of the Y1-R, known to be present in human islets (unlike Y2-R) was also noted for GEP44. Recent evidence points to the protective effect of Y1-R agonism in β-cells, a critical unmet need in current treatment of T2DM, thus making GEP44 an extraordinary monomeric chimeric peptide for achieving polypharmacy in the form of glucoregulation with profound weight loss, β-cell mass protection, and reduced/mitigated nausea/emesis.

Figure 7:
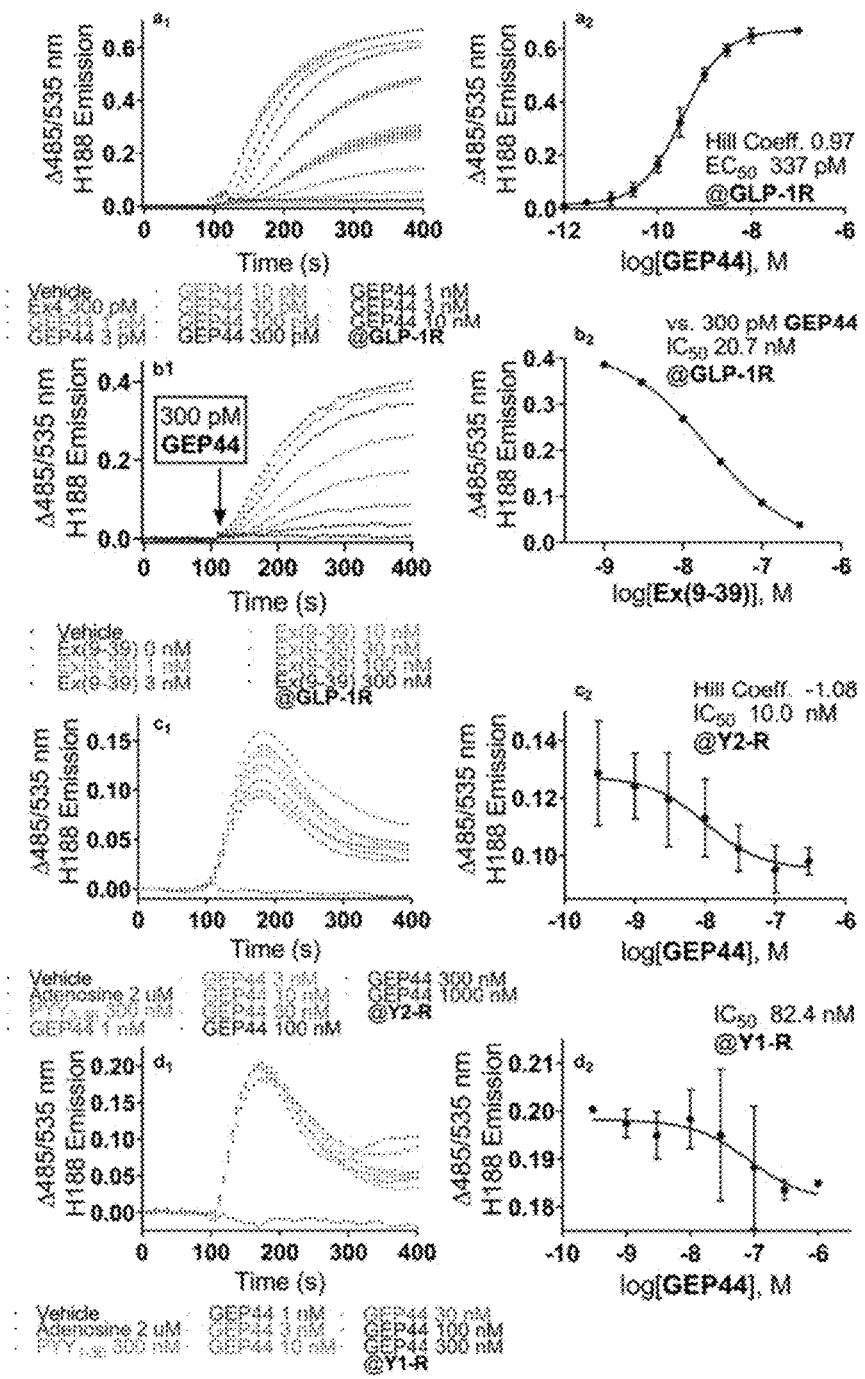
FIG. 7 is a series of graphs of GEP44 signals via the GLP-1R and Y2-R to stimulate cAMP production.

As seen in FIG. 4, preliminary experiments demonstrated feasibility and very strong reduction of FI without induction of nausea assessed by kaolin intake in response to GEP44 (2-d avg. FI: −58% at 10 nmol/kg/d; −84% at 30 nmol/kg/d) vs. Ex-4. Mild reduction of FI was found following EP44 without induction of nausea. As seen in FIG. 7, GEP44 signals via the GLP-1R and Y2-R to stimulate cAMP production.

Insulin secretion and islet viability in response to exposure to chimeric peptides may be evaluated to determine whether EP44 and GEP44 will stimulate ISR at lower doses compared to Ex-4, supporting the therapeutic goal of normalizing blood glucose levels while minimizing nausea. Preliminary data showed that ISR was significantly increased by EP44, GEP44 and Ex-4, as seen in FIG. 3, although to a lesser extent by GEP44. Illustrating the importance of using flow systems to measure real time responses to both stimulation and washout, the effect of Ex-4 was rapidly reversible, whereas the test drugs had sustained effects.

Implications are that short exposure of drug may be enough to stimulate ISR for pharmacologically suitable times (1-2-h after a meal), providing less driving force for symptoms of nausea.

Pharmacokinetic and pharmacodynamic (PK/PD) profiles of several chimeric peptides and their therapeutic windows may be assessed in rats. The drug's effects on food intake, body weight, core temperature, locomotor activity, energy expenditure (EE), and respiratory quotient will be assessed using state-of-the-art techniques. Continuous glucose monitoring may be performed in diet induced obesity as well as lean genetic diabetic rats. The extent to which the GLP-1R contributes to the effects of chimeric peptides on food intake and body weight will be explored in GLP-1R deficient ($Glp1r^{-/-}$) mice. It is believed that the chimeric peptides will exert anorectic and BW reducing effects, mediated by GLP-1R and Y2-R activation, and exert better long-term anorectic and weight reducing effects vs. Ex-4, independent of nausea. Furthermore, these chimeric peptides will likely increase EE as assessed by indirect calorimetry and will exert glucose reducing effects in lean diabetic as well as DIO animals, independent of BW loss.

The present invention thus combines the NPY-R pathways with glucoregulation to produce potent weight-loss, maintain β-cell mass, with reduced incidence of gastric disturbance and malaise. The present invention, including GEP44, may yield therapeutic candidates which will target both energy homeostasis relevant for pharmacological approaches to treating obesity, namely energy intake and thermogenesis without nausea, and glucoregulation/diabetes.

In vitro testing of candidates using a customized perifusion system that both maintains islet health while continuously assessing function, i.e. insulin secretion rate, and viability. Chimeric peptides such as those of present invention are believed to exert multi-agonistic properties at both the Y2-R and GLP1-R, with improved pharmacokinetics compared to native gut peptides GLP-1 and $PYY_{3-36}$, and can also be optimized to agonize the Y1-R, Furthermore, these peptides will likely stimulate insulin secretion from isolated islets via GLP-1R agonism and will thus will increase islet cell health via Y-1R agonism, even when exposed to inflammatory stress.

Pharmacokinetic and pharmacodynamic (PK/PD) profiles of several chimeric peptides and their therapeutic windows may be assessed in rats. The drug's effects on food intake, body weight, core temperature, locomotor activity, energy expenditure (EE), and respiratory quotient will be assessed using state-of-the-art techniques. Continuous glucose monitoring may be performed in diet induced obesity as well as lean genetic diabetic rats. The extent to which the GLP-1R contributes to the effects of chimeric peptides on food intake and body weight will be explored in GLP-1R deficient ($Glp1r^{-/-}$) mice. It is believed that the chimeric peptides will exert anorectic and BW reducing effects, mediated by GLP-1R and Y2-R activation, and exert better long-term anorectic and weight reducing effects vs. Ex-4, independent of nausea. Furthermore, these chimeric peptides will likely increase EE as assessed by indirect calorimetry and will exert glucose reducing effects in lean diabetic as well as DIO animals, independent of BW loss.

Figure 8:
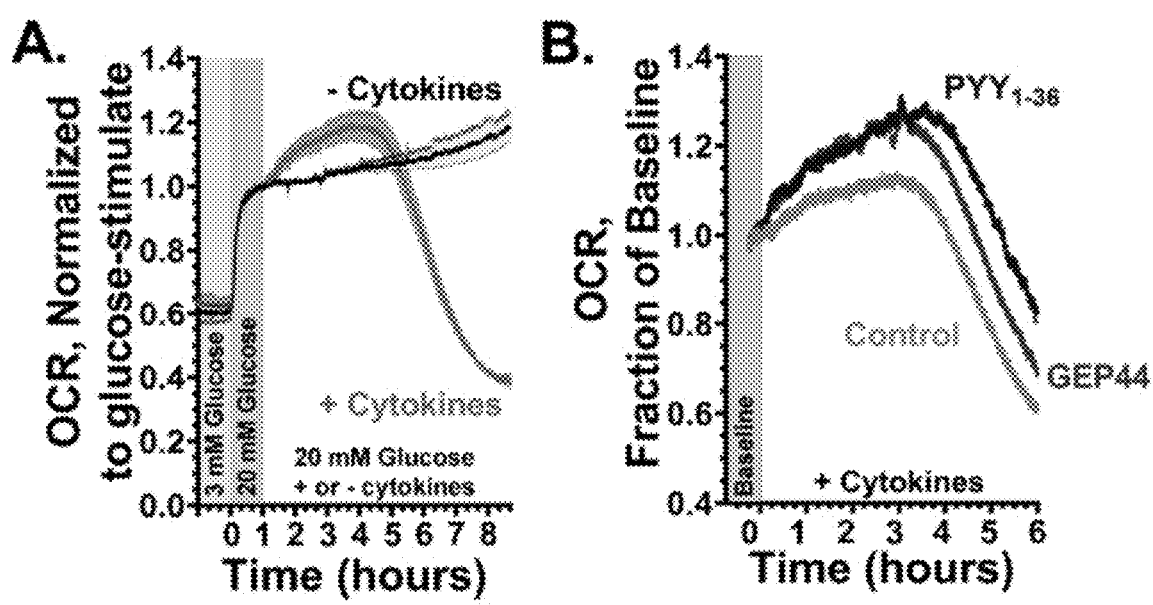
FIG. 8 is a graph of the effect of cytokines (IFN-γ, TNF-α, and IL-1β) on OCR of (A) perifused isolated rat islets; and (B) decreased loss of OCR.

Effects in islet cell perfusion and protection against cytokine induced apoptosis in vitro may be gauged with a customized perifusion system that both maintains islet health while continuously assessing function (insulin secretion rate (ISR)) and viability (oxygen consumption rate (OCR)). OCR is a particularly informative readout reflecting both live cell number and function. By measuring OCR in real time, the actual cell loss due to apoptosis is tracked while enabling assessment of glucose-sensitivity intrinsic to a normal β-cell. In particular, flow measurement of OCR can quantify subtle losses of function and viability needed to characterize drugs at pharmaceutically relevant levels. For this evaluation, a customized perifusion system was used that both maintains islet health while continuously assessing β-cell viability by OCR. A cocktail of cytokines initially led to an increase in OCR, which then fell precipitously by about 60% after 5 hours (FIG. 8A), providing a robust signal with which to assess protective effects of the drugs. Both $PYY_{1-36}$ and GEP44 slowed the fall in cytokine-induced OCR, primarily by leading to a greater initial increase in OCR following the cytokine exposure (FIG. 8B).

The testing of peptides may be performed relative to Ex-4 with both rat and human islets. Islets will be perifused at low glucose and then at 2, 6, 10, 26, 30 and 34-h, glucose will be elevated for 1-h to 10 mM, plus or minus either EP44, GEP44, one lead TBD and Ex-4 for 30 min. Fractions will be collected for ISR determinations and OCR will be assessed continuously for 40-h, a duration designed to resolve both acute and chronic regulation of mechanisms mediating ISR. Based on historical reproducibility, 3-4 experiments will be carried out (with two channels/per experiment) to establish statistical significance of therapeutically meaningful changes (≥20%). Initially, we will use the same concentration for each drug as they have similar attributes for side effects. If ISR stays elevated while glucose is elevated, the duration of drug exposure will be decreased until waning is observed. We will confirm that the test drugs do not increase ISR at low glucose (similar to GLP-1 and Ex-4) to minimize the risk for hypoglycemia in vivo. Based on prior studies, potentiation of glucose-stimulated ISR during exposure of the chimeric peptides is expected. In contrast to Ex-4's effect, which will wane after the washout at 30 min, the effect of EP44 and GEP44 will continue as long as glucose is elevated. Previous studies indicate that the acute effects of GLP-1 and Ex-4 on OCR are small. However, over the course of 2 days, OCR might increase relative to controls indicating upregulation of metabolic pathways or smaller loss of β-cells indicating protection of islets by the drug. Alternatively, OCR could decrease suggesting harmful effects.

The protection by chimeric peptides of immune-mediated damage to islets may be determined using a validated model of immune mediated damage to islets by exposing isolated islets to a mixture of the cytokines IFN-γ, TNF-α, and IL-1β resulting in activation of apoptosis. Islet Y1 receptors are functionally conserved and novel targets for the preservation of β-cell mass.32 Quantifying the decline in OCR as a reflection of loss of viability yields an objective measure of islet damage. The chimeric peptides should prevent islet stress and toxic responses induced by acute cytokine exposure. Preliminary data shows the ability of amino acids to rescue damage induced by a 2-h bout of hypoxia. The fall and recovery of both OCR and ISR were well-resolved, irreversible and reproducible. A time course of decline in OCR in response to the cytokine cocktail mixture may also be used. This data shows an initial increase in OCR (presumably associated with increased energy used in the processes of apoptosis and/or mitochondrial uncoupling) followed by a precipitous decline in OCR. This data corresponds to viability staining carried out the next day (data not shown), but the OCR readout provides a much more sensitive readout. Thus, the foundation is laid to be able to test a drug's ability to slow or prevent the decline in OCR, a critical goal of therapeutic intervention being developed. Testing of EP44, GEP44 and one additional lead vs. Ex-4 with both rat and human islets may be performed by treating islets will be treated for 24-h with these test compounds, followed by an immune stress test consisting of exposure and subsequent washout of the cytokine mixture. ISR and OCR will be assessed throughout the experiment to determine changes in ISR and OCR in response to cytokine as a percent of the decrements with vs. without drug pretreatment (i.e. presence of cytokines alone), change in AUC and the decay half time. Consistent with the hypothesis, pre-treatment with the chimeric peptides should slow the decline in OCR and ISR in response to cytokines. Whether the drugs will be more or less efficacious than Ex-4 cannot be predicted. To distinguish between two possible mechanisms, it is necessary to measure both function and viability. If the effects of a test compound on OCR are correlated with its effects on ISR, this would indicate that prevention of the loss of viable β-cells is mediating the maintenance of secretory function. It is also possible that the test drugs do not prevent the loss of ISR, and yet prevent the loss of OCR. This is because loss of ISR can be temporary while loss of viability is permanent.

Testing of the monomeric peptides on food intake, body weight gain and EE may also be performed. A successful GLP-1R/Y-R dual chimeric agonists is dependent upon an improved therapeutic window, PK profile, and long-term efficacy relative to the constituent peptides. Given that $PYY_{3-36}$ has shown little therapeutic potential due to its short half-life, whereas Ex-4 has robust effects on glucoregulation and FI, comparisons of the chimeric peptides will focus on Ex-4 alone.

A first study may assess the PK/PD profiles of several chimeric peptides as an initial evaluation of the therapeutic potential of each drug as an obesity treatment with a focus on establishing tolerability during sub-acute administration. Results of these initial experiments will be used to determine lead compounds for sub-chronic treatment testing and assessments of energy homeostasis and glucoregulation. Finally, knockout mice will be used to investigate the relative magnitude of effect that is due to GLP-1R agonism by the chimeric peptides across their therapeutic window. The experiments from this study may be performed in DIO Wistar rats (modeling the most common form of obesity and obesity-related impaired glucose metabolism), Goto-Kakizaki rats (a lean model of T2D bred from the Wistar strain), and GLP-1R KO mice. To generate the DIO rats, young Wistar rats (~4-weeks of age) will be placed on a high-fat diet (60% kcal from fat; D12492, Research Diets, Inc., New Brunswick, NJ) for 4-mo prior to the start of testing. 152,153 For all studies, treatment groups will be matched for BW gain and FI profiles with secondary consideration given to fasting blood glucose and lee adiposity index. In all studies, a loss of body weight >30% from pre-treatment in DIO rats constitutes a humane treatment endpoint in accordance with our IACUC approved protocol. Unless otherwise noted, group size will be n=8 animals for all animal experiments.

Another study may establish therapeutic window, pharmacokinetics, and acute effects on FI, BW, and nausea. The tolerability of a drug must be the primary factor in dose selection for treatment in animals. Establishment of the dose-response relationship targeted outcomes within the range to tolerability is essential for evaluation of novel therapies. The chimeric peptides of the present invention are expected to exert anorectic and weight reducing effects independent of nausea. Preliminary dose escalation studies showed remarkable reductions in FI (>88% reduction) following GEP44 administration with no indication of nausea. Conversely, doses of Ex-4 which yielded significant reductions in FI appear to be at the expense of inducing nausea with increases in kaolin intake in proportion to reductions in chow consumption. While these findings are exciting, more in-depth characterization of their dose-dependent effects are necessary in more treatment-relevant animal models. To assess the therapeutic window of chimeric peptides (such as EP44 and GEP44), in vivo determination of a minimum effective dose (MED), a no observed adverse effect level (NOAEL), and a maximum tolerated dose (MTD) in male rats during a 3-d-treatment dose escalation study may be performed. Conditioned taste aversion (CTA) studies will be used as a more sensitive assessment of nausea as a complementary study to the kaolin intake data in the determination of pica behavior. PK testing will provide assessment of the rates of absorption and metabolism of the peptides to aid in determining if alternative dosing strategies are warranted. As Ex-4 has been shown to yield an increase in heart rate and blood pressure in rats (ref), implanted telemetry devices can be used to assess cardiovascular safety at the MTD. Finally, the long-term NOAEL dose for each dual agonist will be established. These tests will allow us to pre-screen candidate drugs before moving to testing in more complex and long-term studies. Initial experiments assessing the compounds' therapeutic windows and CTA at the MTD will utilize male rats to minimize confounding variables during short-term testing. All further testing, including PK and PD studies, will utilize male and female rats for a better assessment of each compound's therapeutic potential. All treatments will be administered once daily, just prior to the start of the dark cycle via subcutaneous (sc) injection.

A dose-escalation study of the lead GLP-1R/NPY-R chimeric multi-agonists and Ex-4 may be performed as a primary assessment of their efficacy in reducing food intake and body weight gain. The testing paradigm used for this study will consist of successive rounds of a 3-d baseline phase (vehicle injections) and a 3-d treatment phase similar to the preliminary studies (see FIG. 3); washout days will be used between testing rounds until BW gain and FI re-stabilizes. Treatment may begin with a low dose (0.2 nmol/kg) based on prior testing with similar peptides and will be increased at approximately third-log increments (e.g. 0.2, 0.5, 1, 2, 5, 10, 20, etc.) until a MTD is reached. Food and kaolin consumption (for assessment of pica behavior) will be continuously recorded while BW and water intake will be measured daily. In addition, infrared cameras may be used to assess behavioral changes for determination of the NOAEL and MTD.(ref) Fasting (6-h) blood glucose will be obtained at baseline and 24-h after the $3^{rd}$ treatment in each testing round.

Figures 9A, 9B:
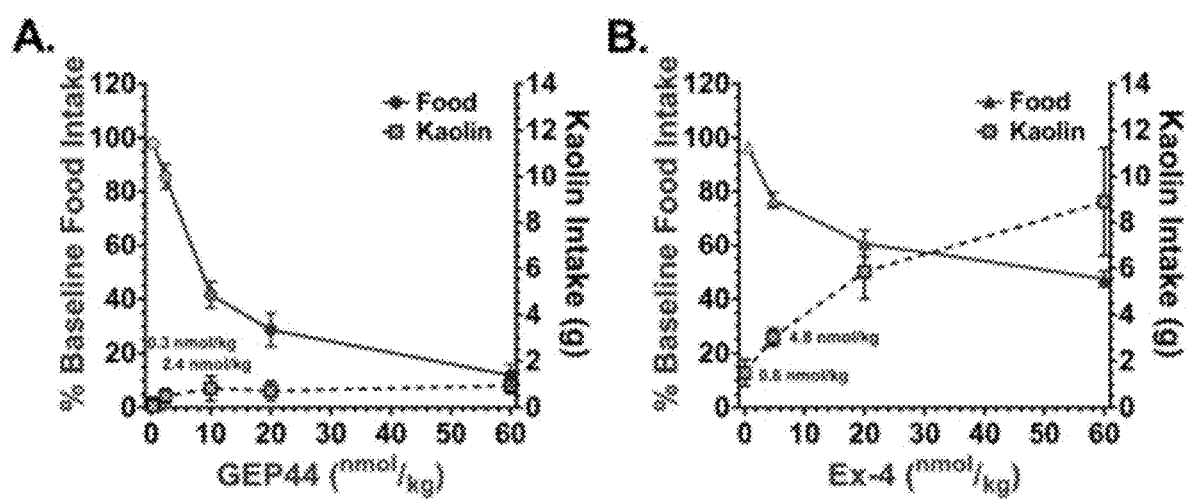
Figures 9C, 9D:
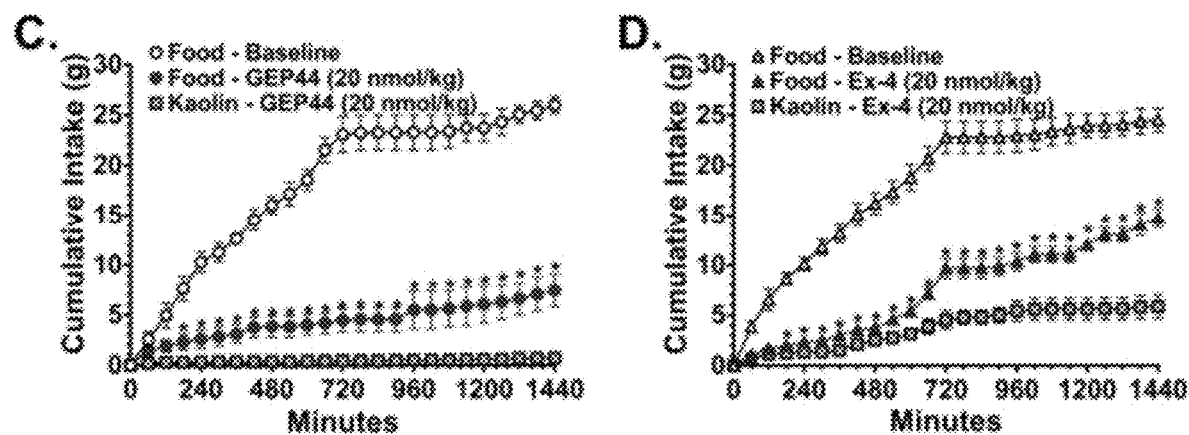
Figures 9H, 9I:
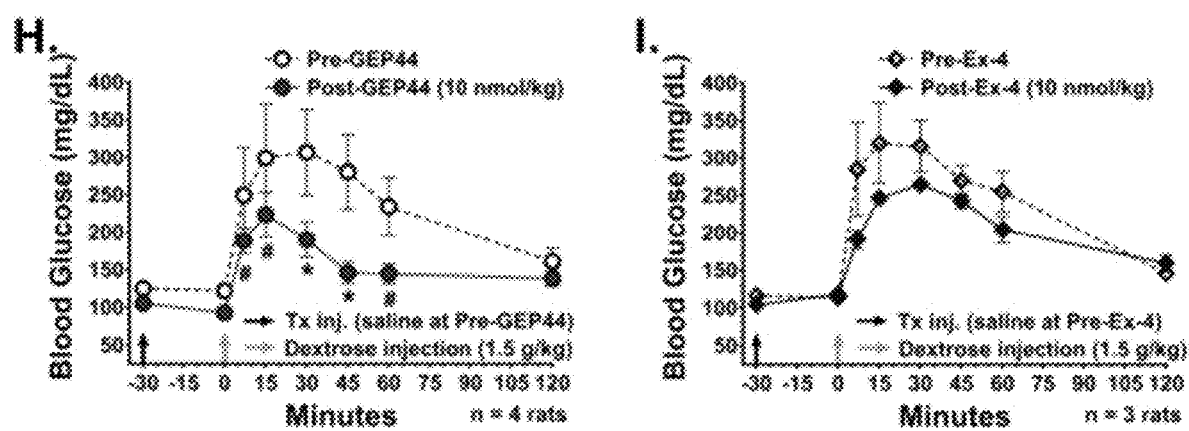

For example, dose escalation studies in lean Sprague-Dawley rats, revealed remarkable reductions in food intake (−81.4% reduction over 2 days) following GEP44 administration (20 nmol/kg daily), with no indication of nausea as monitored by pica. Conversely, doses of Ex4 that yielded significant reductions in food intake were accompanied by significant nausea as reflected by increases in kaolin intake in proportion to reductions in chow consumption (FIG. 9A-D). The absolute lack of an observed pica response for GEP44, in stark contrast to that observed in a dose dependent manner for GLP-1R agonists supports the idea that co-activating NPY receptors along with GLP-1R results in modified signaling compared to each receptor alone, as recently suggested for co-administered $PYY_{3-36}$ and Ex4. Further studies in diet-induced obese Sprague-Dawley rats yielded similar reductions in food intake (FIG. 9F) to the GEP44 dose escalation study, above, with sustained weight loss (FIG. 9E) and a significant reduction in fasting blood glucose (FIG. 9G). Changes in fasting blood glucose are likely due to glucoregulatory effects of GEP44 as the treatment period was too short for changes in body weight to significantly impact metabolism. A 5-d intraperitoneal glucose tolerance comparing GEP44 (FIG. 9H) to Ex4 (FIG. 9I) in pre-diabetic rats was conducted and resulted in stronger reductions in blood glucose for GEP44 compared to Ex4.

To further characterize any treatment associated pica response, CTA studies may be performed at the NOAEL dose for each tested drug. CTA testing will be performed using the KoolAid® flavored chow paradigm, and LiCl will be used as a positive control. Consumption of powdered chow will be continuously recorded using Diet cages (Omnitech Electronics, Inc.).

PK/PD testing will be performed for each treatment and dose tested above in both male and female rats. Serial blood samples will be collected from fasted (4-h prior to injection), un-restrained rats via tail-vein bleeding before and at 0.25, 0.5, 1, 2, 4, 6, 8, and 24-h after sc injection. To assess cardiovascular safety, animals will be implanted with telemetry devices (Indus Instruments) prior to the start of the experiment for continuous assessment of electrocardiogram (ECG), heart rate, activity, and core temperature. For PK testing, chimeric peptide serum concentrations will be assessed. PD outcomes will include blood glucose and serum insulin as well as ECG and heart rate. Assessment of corrected QT from ECG measurements will be corrected for blood glucose and insulin as well as activity. PD outcomes will be factored into the NOAEL and MTD designations as necessary.

Studies may also be performed to assess the effects of subacute treatment at the NOAEL on energy homeostasis and glucoregulation in both sexes. Each of the GLP-1R/NPY-R chimeric multi-agonists and Ex-4 may be further tested in both male and female rats (n=12 rats per sex per group) in a 14-d treatment study at the 3-d NOAEL dose. Testing will be consisting of a 7-d baseline phase (vehicle injected) and a 14-d treatment phase. A staggered-start design may be used for this study so that if adverse effect is encountered it is possible to reduce the dose for the rest of the animals and establish a 14-d NOAEL. A subset of animals from each group (n=6 per treatment per sex) will be implanted with a DSI HD-XG telemetry device for continuous assessment of blood glucose and measures of EE (i.e., gross locomotor activity, core temperature); 10-d of recovery will be given before starting the experiment. An oral glucose tolerance testing (OGTT; 2 g/kg dextrose via oral gavage) and ITT (0.5 IU/kg ip human insulin bolus) will be performed prior baseline phase and end of the 14-d treatment after 6-h fasting. Food and kaolin consumption will be continuously recorded while body weight and water intake will be measured daily. Infrared cameras will be utilized to assess behavioral changes for determination of the 14-d NOAEL using the same criteria as above. The study should show treatment related changes in food intake, body weight, and blood glucose AUC following glucose or insulin bolus at the 14-d NOAEL dose for each chimeric peptide in each sex. It is expected that these experiments will establish an in vivo dose-response model for each peptide that outlines its efficacy in reducing FI and BW along with treatment induced changes in pica behavior and cardiovascular health in a DIO rat model. Additionally, detailed PK profiles of candidate(s) with improved T½, Tmax, Cmax, initial efficacy and duration of response relative to Ex-4 will be established as well as the magnitude of effect of each chimeric peptide on FI, BW, and glucoregulation at the 14-d NOAEL.

A study may be performed to determine long-term treatment effects on FI, BW, nausea, and metabolic health. This study may test two chimeric peptides vs. Ex-4 on subchronic treatment outcomes using pair-fed animals as a control. The monomeric chimeric peptides of the present invention should exert better long-term anorectic and BW reducing effects compared to Ex-4, at doses independent of nausea. While pilot data indicates a significant sub-acute reduction in FI and BW gain due to chimeric agonists treatment, see FIG. 8, relative to vehicle, these studies were performed in lean animals. For initial experiments, dose selection and administration routes for the initial in vivo efficacy studies were based on published data of Ex-4. A dose of GEP44 may be selected to a) gain insight into the initial efficacy/safety correlation, b) attain a direct comparison with the Ex-4 data, and c) evaluate the FI effect of GEP44 during subacute 10-d treatment. In addition to Ex-4 and the two chimeric peptide treatment groups, there would be three vehicle treated groups, weight matched and pair-fed to the three drug treatment groups, and a vehicle treated group. Animals would be assessed for FI, water, and kaolin intake as well as changes in BW during a 7-d baseline (vehicle treated) and 42-d treatment period. Equimolar doses would be used for all treatments, and the treatment doses will be set to 50% of the 14-d NOAEL of Ex-4 determined above. Blood samples will be obtained to correlate dosing and therapeutic effects vs. circulating metabolic and inflammatory biomarkers at three time-points: prior to the start and at the end of treatment as well on treatment day 4 to assess treatment induced changes before major changes in BW might occur. Post-treatment, animals will be sacrificed, and pancreatic tissue will be collected for islet cell histology. Determinations of lean body mass and fat mass will be made on carcasses by quantitative magnetic resonance using an EchoMRI 4-in-1™700 instrument. Primary outcomes will be changes in FI and BW. Changes in fasting glucose, insulin, leptin and inflammatory biomarkers (IL-6, IL-1β, and TNF-α), transaminases ALT and AST as well as triglycerides, HDL and LDL cholesterol will be assessed. Additionally, cross-sectional differences in islet cell morphology and body composition may be assessed. The study should identify an optimized chimeric peptide with significantly stronger weight loss relative to Ex-4. Additionally, there should be a reduced attenuation of treatment efficacy with the chimeric peptides, as compared to Ex-4, due to the activation of synergistic pathways. Additionally, a lower reduction in BW among pair-fed animals would indicate an effect of the treatment on EE. If there are changes of transaminases, it is possible to consider scoring liver tissues for changes in fatty liver disease.

A study may be performed to determine the effects of chimeric peptides on measures of energy homeostasis (energy expenditure (EE), locomotor activity, core temperature, food intake, body adiposity, and body weight). Chimeric peptides of the present invention should increase EE as assessed without inducing a change in locomotor activity. Based on previous studies that indicate GLP-1 or the GLP-1R agonists increase activation of IBAT, increase IBAT temperature, or increase thermogenic gene expression in IBAT (UCP-1, DIO2, PGC1alpha and FGF21), the impact of the chimeric peptides on EE relative to Ex-4 may be determined. All drugs will be tested at equimolar doses set at the lowest NOAEL of selected drugs from above. All rats (adult male and female DIO Wistar IGS rats; N=8/sex) will have their body composition measured once after a 4-mo prolonged exposure to high fat diet (HFD) and again at the end of treatment. DIO rats will be implanted with a transponder device in the intraperitoneal cavity to enable measurements of core temperature and gross motor activity. Following recovery, rats will be placed in the VAPSHCS Rodent Metabolic Phenotyping Core (RMPC) metabolic cages [(Comprehensive Laboratory Animal Monitoring System (CLAMS)]. Testing will occur over a 4-week treatment period during which time we will obtain daily food intake and body weight, core temperature, EE, respiratory quotient (RQ), locomotor activity measurements. These measurements will be taken in 4 h fasted rats to prevent the potential confounding effects of diet-induced thermogenesis on measures of EE. At study completion, 4 h fasted animals will be injected with chimeric peptides or vehicle. A subset of animals will be perfused with 4% paraformaldehyde (PFA) so that brains and IBAT/TWAT can be processed for analysis of Fos and 3,3'-Diaminobenzidine (DAB), respectively. The other subset of rats will have IBAT and TWAT immediately flash frozen in liquid nitrogen for gene expression analysis of thermogenic markers (UCP-1, DIO2, FGF21 mRNA).

EE, RQ and LA will be assessed using indirect calorimetry available using the CLAMS through the VAPSHCS RMPC (Columbus Instruments, Columbus, OH). Body fat mass and lean mass may be determined using Quantitative Magnetic Resonance (QMR) at the RMPC at the VAPSHCS. IBAT and TWAT will also be collected from perfused animals, post-fixed overnight in 4% PFA, and processed for paraffin embedding prior to staining for UCP-1 protein. Microtome sections (5 µm) will be stained with DAB. Chimeric peptides should increase EE without inducing a change in LA. Such a result would raise the interesting possibility that the chimeric peptides induce BAT thermogenesis.

A study may be performed to assess central (i.e. hypothalamic/hindrain) GLP-1R and Y2-R binding using fluorescently labeled peptides in combination with Fos colocalization. Circulating $PYY_{3-36}$ and Ex-4 inhibit FI via activation of Y2-Rs and GLP1-Rs in the brain respectively. Peripheral administration of $PYY_{3-36}$ increases Fos in areas linked to the control of food intake [ARC, DMN, PVN, AP, NTS and dorsal motor nucleus of the vagus (DMV)] and where Y2-Rs are expressed. While systemic administration of Ex-4 has been associated with elevated Fos in areas linked to the control of food intake where GLP-1Rs are expressed, at doses that are not associated with aversive effects, it also elevates Fos in the NTS at doses associated with aversive effects. Similarly, Ex-4 binding in the mNTS has been implicated in a nausea effect. Fluorescent labeled chimeric peptides may be used to assess whether these peptides cross the BBB and are colocalized in mediobasal hypothalamic and hindbrain neurons that show elevated Fos in response to peripheral administration of these chimeric peptides and are known to express GLP-1R and Y2-R. Pending a positive finding from these studies, future studies will assess if fluorescence and Fos induction are colocalized with GLP-1R, Y2-R, and Y1-R in the mediobasal hypothalamus (ARC, PVN, DMN, VMN) and hindbrain (AP, DMV, and NTS).

Specifically, fasted animals will be injected with chimeric peptides or vehicle. After 2 h under deep sedation, they will be perfused transcardially with ice-cold saline followed by ice-cold 4% PFA. Brains will be harvested, placed in 25% sucrose for 48 h, frozen in isopentane, cryostat sectioned (14 µm) and stored frozen until time of immunocytochemistry (ICC) assay. Tissue will be stained for Fos and analyzed for colocalization with fluorescent labeled chimeric peptides. All antibodies have been tested and used successfully for immunostaining for Fos. Image analysis software in conjunction with microscopy will be used for data analysis. All analyses will be compared at identical levels for treatment effects above background. Fos (+) cells will be denoted by nuclear immunostaining with Cy3 as previously described. Fluorescence staining of drug conjugates will be denoted by staining with Alexa 488 dyes that are excited by confocal lasers.

A study may be performed to determine the effects of chimeric peptides vs. Ex-4 on glucose tolerance and metabolic outcomes in GOTO-KAKIZAKI lean diabetic rats. Preliminary islet cell perfusion results demonstrate stimulation of insulin secretion by our chimeric peptides (EP44 effects >GEP effects) in vitro, and first results show reduction of glucose levels following acute EP44 injection in vivo, as seen in FIG. 10. Evaluation of glucose stimulated insulin secretion (GSIS) by rat pancreatic islets in response to GEP44 was performed in vitro, as seen in FIG. 11. GSIS was significantly increased by GEP44 and Ex4, but not by PYY1-36 or PYY3-36, confirming that the increase of GSIS by GEP44 is driven by stimulation of islet GLP-1Rs.

Testing of GEP44 in a mammal model also demonstrated favorable results. More specifically, testing of GEP44 in shrews demonstrates that there is no vomiting (rodents can't vomit, but shrews can). As seen in FIG. 12, administration of GEP44 in shrews confirmed glucoregulation (IPGTT) and demonstrates little/no vomiting (emesis).

Finally, as seen in FIG. 13, testing of GEP44 in rats showing a reduction in the drive to obtain fentanyl when provided at doses lower than exendin-4. Thus, at doses less than those that might cause weight loss (typically <2.4 ug/Kg), GEP44 may also be effective for the treatment of addiction, such as treatment of dependency on opioids, cocaine, etc.

Further studies could examine the intriguing possibility that chimeric peptides (in particular EP44) can improve or normalize diabetic blood glucose levels without any impact on BW which has a high translational value for treatment of lean subjects with diabetes. This study would further assess the glucoregulatory effects of the lead chimeric peptides vs. Ex-4 independent of weight change utilizing Goto-Kakizaki rats in a dose escalation study. Each rat will be implanted with a DSI HD-XG telemetry device for continuous assessment of blood glucose and measures of EE (i.e., locomotor activity, core temperature); 10-d of recovery will be given before starting the experiment. This study will consist of a 7-d baseline phase followed by a dose escalation phase where each dose is administered for two consecutive days with an OGTT performed on the second day; a 2-d washout/recovery phase will be used between doses. Treatment groups will consist of n=4 animals per sex and treatments will begin with a low dose (0.2 nmol/kg) based on prior testing with similar peptides and will be increased at approximately third-log increments (e.g. 0.2, 0.5, 1, 2, 5) for 5 dose rounds or until the 14-d NOAEL from DIO animals is reached. All treatments will be administered once daily prior to the start of the dark cycle, via sc injection. Animals will be tested for changes in FI, BW, and water intake. Treatment with chimeric peptides should exhibit an increased activity relative to Ex-4 in vitro will also yield greater improvements in glucose metabolism in vivo.

Finally, a study may be performed to determine contribution of GLP-1R- vs. Y2-R-mediated effects in vivo using receptor knock-out models. Chimeric peptides should fail to increase EE in both male and female DIO Glp1r−/− mice but should stimulate EE in male and female littermate control mice (as assessed by indirect calorimetry) without inducing a change in locomotor activity or body temperature. This is an exploratory proof-of-principle study, which might need require follow-up studies geared towards understanding the mechanisms of chimeric peptides acting via two or more receptor pathways. The study aims first to test whether responses to two lead chimeric peptides (GEP44 and EP44 or another peptide vs. Ex-4) on FI, BW change, and EE are different in adult male Glp1r−/− mice vs. age-matched littermate control mice. Adult male and female DIO Glp1r−/− mice and littermate control mice will be used to assess the overall effects or the relative proportion of a shared effect that is due to GLP-1R vs. Y2-R agonism by select chimeric peptides. As the proportion of effect due to GLP-1R or Y2-R agonism is likely to change with dose, this study will evaluate the selected peptides at each of the doses used in the therapeutic window experiment. Mice will be maintained on HFD for 4-mo. after which time it is possible to obtain body composition measurements to confirm DIO. During week 1, mice will receive 1× daily sc injections of chimeric peptides or Ex-4 with all drugs to be tested at equimolar doses. Successive rounds of testing will consist of a 2-d baseline phase and a 2-d treatment phase with 3-d of washout in between. Core body temperature and gross motor activity will be assessed via an implanted telemetry device. Testing will occur over a 4-week treatment period during which time we will obtain daily BW, food, water and kaolin intake. At study completion, mice will undergo a 4-h fast followed by sc treatments 2-h prior to euthanasia, after which time tail vein glucose (before anesthesia), brains, TWAT, IBAT, and blood (by cardiac stick; after anesthesia) will be collected. A subset of mice will be perfused with 4% PFA for analysis of Fos in the mediobasal hypothalamic (ARC, PVN, DMH, VMH) and hindbrain sites (AP, DMV, and NTS) that show elevated Fos in response to $PYY_{3-36}$, Ex-4 or both and are known to express GLP-1Rs and Y2-Rs. Blood will be processed for descriptive measures (leptin, insulin, glucose, total cholesterol, triglycerides, free fatty acids, glycerol and lipids). Chimeric peptides are expected to exert FI and BW reduction in Glp1r−/− mice, but this effect will be significantly weaker compared to WT mice indicating that the drug's effect cannot be entirely explained by GLP-1R effects potentially due to contribution of Y2-R. If that is the case, future experiments may also test Y2-R−/− mice to verify this effect.

EXAMPLE

Materials and Methods

Materials. Novel chimeric peptides (GEP44 and EP series) were produced by Genscript (Piscataway, NJ) with C-terminal amidation and K12-azido modification. Purity and identity were confirmed in-house by reversed-phase HPLC and electron spray MS, respectively. GLP-1, glucagon, Ex4, Ex(9-39), $PYY_{3-36}$, and adenosine were from Sigma. BIIE0246[43] was obtained from Tocris Biosciences (Minneapolis, MN).

Cell culture. The parental HEK293 cell line was obtained from the American Type CultureCollection (ATCC, Manassas, VA). HEK293 cells stably expressing the human GLP-1R at a density of 150,000 receptors/cell were obtained from Novo Nordisk A/S (Bagsvaerd, Denmark). HEK293 cells stably expressing H188 were generated by O. G. Chepurny in the Holz laboratory[52]. All cell cultures were maintained in Dulbecco's modified Eagle's medium containing 25 mM glucose and supplemented with 10% fetal bovine serum and 1% penicillin/streptomycin. Cell cultures were equilibrated at 37° C. in a humidified incubator at 5% $CO_2$ and passaged once a week. Culture media and additives were obtained from ThermoFisher Scientific (Waltham, MA).

Cell transfection. Transient transfections were performed using Lipofectamine and Plus Reagent (from ThermoFisher Scientific) using the methodology described previously by the Holz laboratory for HEK293 cell[31]. Plasmids encoding human NPY1-R and NPY2-R in pcDNA3.1 were obtained from the University of Missouri-Rolla cDNA Resource Center (Rolla, MO). HEK293 cells stably expressing H188 were obtained by G418 antibiotic resistance selection using methodology described previously[31]. Adenovirus for transduction of HEK293 cells was generated by a commercial vendor (Vira-Quest, North Liberty, IA) using the shuttle vector pVQAd CMV K-NpA and the H188 plasmid provided by Prof. Kees Jalink.

FRET reporter assay in a 96-well format. HEK293 cells stably expressing recombinant GPCRs were plated at 80% confluence on 96-well clear-bottom assay plates (Costar 3904, Corning, NY). Cells were then transduced for 16 h with H188 virus at a density of 60,000 cells/well under conditions in which the multiplicity of infection was equivalent to 25 viral particles per cell. The culture media were removed and replaced by 200 µL/well of a standard extracellular saline (SES) solution supplemented with 11 mM glucose and 0.1% BSA. The composition of the SES was (in mM): 138 NaCl, 5.6 KCl, 2.6 $CaCl_2$, 1.2 $MgCl_2$, 11.1 glucose, and 10 HEPES (295 mosmol, pH 7.4). Real-time kinetic assays of FRET were performed using a FlexStation 3 microplate reader equipped with excitation and emission light monochromators (Molecular Devices, Sunnyvale, CA). Excitation light was delivered at 435/9 nm (455 nm cutoff), and emitted light was detected at 485/15 nm (cyan fluorescent protein) or 535/15 nm (yellow fluorescent protein)[31,54,55]. The emission intensities were the averages of 15 excitation flashes for each time point per well. Test solutions dissolved in SES were placed in V-bottom 96-well plates (Greiner Bio-One, Monroe, NC), and an automated pipetting procedure was used to transfer 50 µL of each test solution to each well of the assay plate containing monolayers of these cells. The 485/535 emission ratio was calculated for each well, and the mean±SD. values for 12 wells were averaged. These FRET ratio values were normalized using baseline subtraction so that a y-axis value of 0 corresponds to the initial baseline FRET ratio, whereas a value of 100 corresponds to a 100% increase (i.e. doubling) of the FRET ratio. The time course of the FRET ratio was plotted after exporting data to GraphPad Prism 8.1 (GraphPad Software, San Diego, CA). Prism 8.1 was also used for nonlinear regression analysis to quantify dose-response relationships.

Circular Dichroism. Peptides for circular dichroism (CD) were constituted at 35 M in non-supplemented standard extracellular saline (SES) solution at pH 7.4 (FIG. 1B). CD measurements were obtained in triplet with a JASCO J-715 Spectropolarimeter at 25 C using a 1 cm quartz cell, 250-215 nm measurement range, 100 nm/min scanning speed, 1 nm bandwidth, 4 s response time, and 1.0 nm data pitch. The measured triplets were averaged, baseline subtracted, and smoothened by ProData Viewer software. The CD measurements were converted to the molar ellipticity (Equation (1)), then to percent helicity (Equation (2)).

$$\text{Molar Ellipticity } [\odot] = \frac{(A * M * 3298)}{(L * C)} \quad (1)$$

$A = \text{Absorbance (Abs)}$
$C = \text{Concentration (g/L)}$
$M = \text{Average Molecular Weight (g/mol)}$
$L = \text{Path Length of Cell (cm)}$ $$\text{Percent Helicity } [\%] = \frac{\left(\frac{\Theta * 100}{(39500 * (1 - 2.57))}\right)}{n} \quad (2)$$

$n = \text{Number of Residues}$

PEP-FOLD3, Simulated Secondary Structure Prediction. The PEP-FOLD3[33] de novo peptide structure simulating software was used to predict secondary structure for the chimeric peptides screened herein (FIG. 1C). PEP-FOLD3 has drawn attention as an on-line tool to simulate models of peptides from 5 to 50 amino acids and has proven useful to chemist and biologist. Primary aim of utilizing PEP-FOLD3 focused on observing alpha helical secondary structure and formation of the desired PP-Fold' (FIG. 1C, FIG. S2).

HPEP-DOCK, Protein-Peptide Docking Prediction. The PDB files obtained from the PEP-FOLD3 simulations were input into HPEP-DOCK[37] blind protein-peptide on-line docking server to simulate docking for each chimeric peptide with the extracellular domain (ECD) of the targeted receptors GLP-1 (PDB: 3IOL), Y2 (PDB: 2IK3), and Y1 (PDB: 5ZBQ). The HPEP-DOCK server utilizes a hierarchical docking protocol that accepts sequence and structure as input for both protein and peptide. Outputs from HPEP-DOCK received a Z-score for binding energy and were analyzed in PyMOL to evaluate protein-peptide interactions, or lack thereof, within the binding domain. Primary aim for HPEP-DOCK targeted establishing a Z-score comparable to the native substrates and known interactions between Ex4 and the ECD of GLP-1R (FIG. S3).

Animal Experiments. All procedures were approved and conducted in compliance with US federal law and institutional guidelines, are congruent with the NIH guide for the Care and Use of Laboratory Animals and are approved by the Seattle Children's Research Institute or University of Washington Institutional Animal Care and Use Committee (SCI Protocol IACUC00064; UW Protocol 409101)

Dose Escalation Study. Lean Sprague Dawley rats (350 g) were individually housed in cages capable of recording food intake (Accuscan Diet cages). The animal room was maintained on a 12-h light/12-hour dark cycle. The study design consisted of sequential rounds of a 2-day baseline phase, a 2-day treatment phase, and a 2-day washout phase. Body weight was assessed daily just prior to the start of the dark cycle, food and kaolin intake were available ad libitum and consumption was continuously recorded. Treatment doses were administered just prior to the start of the dark cycle via subcutaneous injection.

Diet Induced Obese (DIO) rats. To generate DIO rats, young (4-wk of age) lean male Sprague Dawley rats (Charles River Laboratories, Inc. Wilmington, MA; strain code 001) were placed on a high fat diet (HFD; D12492, 60% kcal from fat, Research Diets, New Brunswick, NJ) for 4-5 months prior to the start of the experiments to attain >20% of body fat. During this time, animals had ad libitum access to food and water.

5-day Treatment in DIO rats. DIO Sprague Dawley rats (2 cohorts; 826.1 g n=9, and 642.3 g n=5) were individually housed and the animal room was maintained on a 12-h light/12-hour dark cycle. During the 5-day baseline phase, animals were administered vehicle (0.9% sterile saline solution, injectable) injections just prior to the start of the dark cycle. At the end of the baseline phase, animals were grouped based on body weight, average daily body weight gain, and food intake. Assigned treatments (Vehicle vs. 10 nmol/kg GEP44 vs. 10 nmol/kg Ex4) were administered once daily just prior to the start of the dark cycle for 5 days. Throughout the experiment, body weight and food intake (via hopper weighs) were assessed daily just prior to the start of the dark cycle. Fasting blood glucose was tested prior to the baseline phase and at the end of the treatment phase via handheld glucometer (One Tough Ultra).

Treatment Induced Changes in Glucose Tolerance in DIO rats. DIO Sprague Dawley rats (803.0±102.7 g n=7) were administered a pre-treatment IPGTT with a vehicle injection. Animals were grouped based on body weight, Lee Index (a measure of adiposity; lee index=weight1/3/nasoanal length), and baseline IPGTT blood glucose excursion. Assigned treatments (GEP44 or Ex4; 10 nmol/kg) were administered once daily just prior to the start of the dark cycle for 5 days. On treatment day 5, a repeat IPGTT was performed with the assigned treatment. All weights noted are mean±Std. Dev.

Metabolic testing. Intraperitoneal glucose tolerance testing (IPGTT) was performed following a 6-h fast such that the glucose bolus occurred at the start of the dark cycle; all animal handling is performed under red light. Baseline blood glucose measures were immediately before administration of assigned treatment (vehicle at pre-treatment IPGTT, 10 nmol/kg GEP44 or Ex4 at post-treatment). A second baseline sample was obtained 30 minutes later, immediately prior to the dextrose bolus (1.5 g/kg dextrose, 20% solution). Additional blood glucose measurements were taken 7, 15, 30, 45, 60, and 120 minutes post-bolus. All blood glucose measurements were made via handheld glucometers (One Touch Ultra) in duplicate; if the variation between the two measures was >5%, a third measurement was taken.

Rat islet isolation and culture. Islets were harvested from Sprague-Dawley rats (approximately 250 g; Charles River) and anesthetized by intraperitoneal injection of pentobarbital sodium (150 mg/kg rat). Islets were prepared and purified as described[56]. Islets were then cultured for 18 h in a 37° C., 5% $CO_2$ incubator prior to the experiments in RPMI medium supplemented with 10% heat inactivated fetal bovine serum (Invitrogen).

Static measurement of ISR. ISR was determined statically with multiple conditions, as described previously[57]. Briefly, islets were handpicked into a petri dish containing KRB, 0.1% BSA, and 3 mM glucose and incubated at 37° C., 5% $CO_2$ for 60 min. Subsequently, islets were picked into wells of 96-well plates containing desired amounts of glucose and agents as indicated and incubated for an additional 60 min. At the end of this period, supernatant was assayed for insulin.

What is claimed is:

1. A chimeric peptide comprising an amino acid sequence comprising SEQ ID NO: 11.

2. The chimeric peptide of claim 1, wherein the chimeric peptide comprises a K12-azido modification.

3. The chimeric peptide of claim 1, wherein the serine at the second position of SEQ ID NO: 11 is a D-isomer of serine.

4. A method of treating a human patient for obesity, the method comprising the step of administering a therapeutic amount of a chimeric peptide of claim 1 to the patient.

5. The method of claim 1, wherein the serine at the second position of SEQ ID NO: 11 is a D-isomer of serine.

6. A method of reducing food intake and weight gain without causing nausea in a human patient, the method comprising the step of administering a therapeutic amount of a chimeric peptide of claim 1 to the patient.

7. A method of treating a human patient for addiction to an opioid, comprising the step of administering a therapeutic amount of a chimeric peptide of claim 1 to the patient.

8. The method of claim 7, wherein the opioid is fentanyl.

9. A method of treating Type II diabetes in a subject in need thereof, comprising administering the chimeric peptide of claim 1 to the subject.

* * * * *